US011083822B2

(12) United States Patent
Smith et al.

(10) Patent No.: US 11,083,822 B2
(45) Date of Patent: Aug. 10, 2021

(54) COMBINATION CELLULOSE MATERIAL AND METHOD OF MAKING SAME

(71) Applicant: ETHICON, INC, Somerville, NJ (US)

(72) Inventors: Daniel J. Smith, Somerville, NJ (US); Christophe Vailhe, Somerville, NJ (US)

(73) Assignee: Ethicon, Inc., Somerville, NJ (US)

( * ) Notice: Subject to any disclaimer, the term of this patent is extended or adjusted under 35 U.S.C. 154(b) by 660 days.

(21) Appl. No.: 15/327,234

(22) PCT Filed: Jul. 17, 2015

(86) PCT No.: PCT/US2015/040847
§ 371 (c)(1),
(2) Date: Jan. 18, 2017

(87) PCT Pub. No.: WO2016/011315
PCT Pub. Date: Jan. 21, 2016

(65) Prior Publication Data
US 2017/0216496 A1    Aug. 3, 2017

Related U.S. Application Data

(60) Provisional application No. 62/026,148, filed on Jul. 18, 2014, provisional application No. 62/026,156, filed on Jul. 18, 2014.

(51) Int. Cl.
*A61L 31/12* (2006.01)
*A61L 31/14* (2006.01)
*A61L 24/00* (2006.01)

(52) U.S. Cl.
CPC .......... *A61L 31/129* (2013.01); *A61L 24/001* (2013.01); *A61L 24/0031* (2013.01); *A61L 24/0042* (2013.01); *A61L 24/0094* (2013.01); *A61L 31/14* (2013.01); *A61L 31/145* (2013.01); *A61L 31/148* (2013.01); *A61L 2300/404* (2013.01); *A61L 2400/06* (2013.01)

(58) Field of Classification Search
CPC ................. A61L 31/129; A61L 31/145; A61L 2300/404; A61L 2300/424
USPC ........................................................ 514/57
See application file for complete search history.

(56) References Cited

U.S. PATENT DOCUMENTS

| | | | |
|---|---|---|---|
| 6,235,726 B1 | 5/2001 | Burns et al. | |
| 2007/0020318 A1* | 1/2007 | Silcock | A61L 15/28 424/445 |
| 2007/0269580 A1* | 11/2007 | Werstak | A23L 29/10 426/634 |
| 2011/0152924 A1* | 6/2011 | Gensini | A61L 15/28 606/213 |
| 2013/0316974 A1* | 11/2013 | Wang | A61L 26/0066 514/57 |

FOREIGN PATENT DOCUMENTS

| | | |
|---|---|---|
| CN | 1531910 A | 9/2004 |
| CN | 101720237 A | 6/2010 |
| EP | 1 493 451 A1 | 1/2005 |
| JP | 2000-513258 | 10/2000 |

OTHER PUBLICATIONS

Kastner et al. (Colloids and Surfaces 123-124 (1997) 307-328).*
International Search Report and Written Opinion dated Oct. 21, 2015 for Application No. PCT/US2015/040847, 7 pgs.
U.S. Appl. No. 62/026,131, filed Jul. 18, 2014.
U.S. Appl. No. 62/026,148, filed Jul. 18, 2014.
U.S. Appl. No. 62/026,156, filed Jul. 18, 2014.
Australian Office Action, Examination report No. 1 for standard patent application, dated Jun. 18, 2018 for Application No. AU 2015289491, 3 pgs.
Australian Office Action, Examination report No. 2 for standard patent application, dated Jul. 18, 2018 for Application No. AU 2015289491, 4 pgs.
Australian Office Action, Examination report No. 3 for standard patent application, dated Aug. 29, 2018 for Application No. AU 2015289491, 3 pgs.
Australian Office Action, Examination report No. 4 for standard patent application, dated Oct. 15, 2018 for Application No. AU 2015289491, 3 pgs.
European Exam Report dated Oct. 16, 2018 for Application No. EP 15754057.6, 5 pgs.
Aqualon®, Sodium Carboxymethylcellulose, Physical and Chemical Properties, Hercules Incorporated, 1999, 32 pgs.
Ashland, "Product Grades Available," copyrighted 2016, Ashland / PC-11608.11, retrieved from the internet Feb. 6, 2019, at https://www.ashland.com/file_source/Ashland/Industries/Pharmaceutical/Articles/PC-11608.11_Pharma_Product_Grades.pdf, 4 pgs.
Chinese Office Action, First Office Action and Search Report, dated Mar. 29, 2019 for Application No. CN 201580039286.7, 13 pgs.
Japanese Office Action, Notification of Reasons for Refusal, dated Feb. 19, 2019 for Application No. JP 2017-502831, 4 pgs.
Japanese Office Action, Decision to Grant a Patent, dated Sep. 24, 2019 for Application No. JP 2017-502831, 2 pgs.
Brazil Office Action dated Aug. 16, 2019 for Application No. BR112017000844-0, 4 pages.
Chinese Office Action, the second Office Action, dated Feb. 3, 2020 for Application No. 201580039286.7, 8 pages.
Chinese Office Action, the third Office Action, dated Jul. 21, 2020 for Application No. 201580039286.7, 8 pages.

* cited by examiner

*Primary Examiner* — Shaojia A Jiang
*Assistant Examiner* — Michael C Henry
(74) *Attorney, Agent, or Firm* — Frost Brown Todd LLC

(57) ABSTRACT

Combination cellulose materials and methods of making and using these materials. The combination material includes a first cellulosic material and a second cellulosic material.

20 Claims, 8 Drawing Sheets
(8 of 8 Drawing Sheet(s) Filed in Color)

COMBINATION CELLULOSE MATERIAL AND METHOD OF MAKING SAME

CROSS-REFERENCE TO RELATED APPLICATIONS

This application claims priority to International Application No. PCT/US 2015/040847, filed on Jul. 17, 2015, the entire contents of which are incorporated by reference herein; U.S. Patent Application No. 62/026,148, filed Jul. 18, 2014, the entire contents of which are incorporated by reference herein; and also U.S. Patent Application No. 62/026,156, filed Jul. 18, 2014, the entire contents of which are incorporated by reference herein.

FIELD OF THE INVENTION

The present invention relates to combination cellulose materials and methods of making and using these materials. The combination material includes a first cellulosic material and a second cellulosic material, combined with each other.

BACKGROUND

Adhesion prevention products currently exist in the form of implantable fabrics or films that create a physical barrier to adhesion formation. These products, however, are difficult to place through small openings and laparoscopic surgeries. To overcome this problem, flowable products in the form of ionic or covalent hydrogels have been investigated. Covalent absorbable hydrogels often create some potential biocompatibility issue since a reactive component is introduced in the human body without guarantee that the chemical crosslinking reaction will be complete, leaving reactive species in-situ.

Polysaccharides are known as candidates for good biological materials, including for adhesion prevention. It is particularly desirable to use such materials in a flowable form, such as a gel, to achieve a good balance between ease of delivery (easily flowable through needle or catheter), efficacy (stay in place and remain a barrier for a period of days) and absorbability (after a desired number of days, the product should be absorbed by the body as quickly and safely as possible). For ionic gels that are easily absorbed, a problem is to achieve maximum ionic crosslinking for the gel to form a continuous barrier and provide good cohesive energy while maintaining the molecular weight of the molecules as low as possible. Previous attempts have typically used materials having higher molecular weight averages. When use of low molecular weight materials is not possible, previous attempts have turned to covalent crosslinking of the gels with hydrolysable entities. Unfortunately, this approach leads to less or non flowable materials and films or fabrics.

One other desirable property usually not found in previous attempts is the ability to adhere to wet tissue so that the product stays where placed by the surgeon without any anchoring or suturing of the product. While some gels, such as cellulose gels, are known to be useful, a mixture of a gel and a solid to achieve a flowable gel is not currently known. For example, a mixture including carboxy methyl cellulose in the form of a gel and oxidized regenerated cellulose in the form of a powder has been used as a dry film, but this concept requires mixing and formation prior to use, and does not result in a flowable product that can be applied by a user in this form. Such films and fabrics are difficult to place through small openings and laparoscopic surgeries.

There is currently a need for a flowable composition having a lower molecular weight that can be prepared by a user and applied to a target site to provide biological benefits. Further, there is a need for a method of preparing such a composition.

SUMMARY

In some aspects, the invention disclosed herein includes a composite material is provided including a first gel component, a second powder component, and an aqueous component, such as water or saline. The composite material may include an additional salt if desired. The first gel component may include a cellulose, such as carboxymethyl cellulose. The CMC desirably has a medium or lower molecular weight average, and is present in the CMC gel in an amount of about 3% to about 6% by weight of the gel. The second powder component may include cellulose fibers, such as oxidized regenerated cellulose in the form of micro-fibers.

The invention also includes a method of forming the composite material is provided, where the second powder component may be first wetted or prepared into a suspension by mixing with the aqueous component, such as water or saline, and then the suspension is mixed with a cellulose gel. An additional salt may be added to the cellulose gel prior to adding the suspension or after adding the suspension. The composite material may be applied to any desired target site, such as a bodily site.

The composite gel-like material may be used as an adhesion prevention material, where the composite material is delivered to a target site intended to reduce adhesions. The composite material may be used as a carrier for other biomedical materials, such as in general surgical purposes or for delivery of radiation or other drug materials. The composite material may be used as an absorbable plug, or to seal or minimize fluid leakage in a bodily site.

The composite material may include additional components, such as anti-bacterial agents, imaging agents, pharmaceutical agents, and combinations thereof.

DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
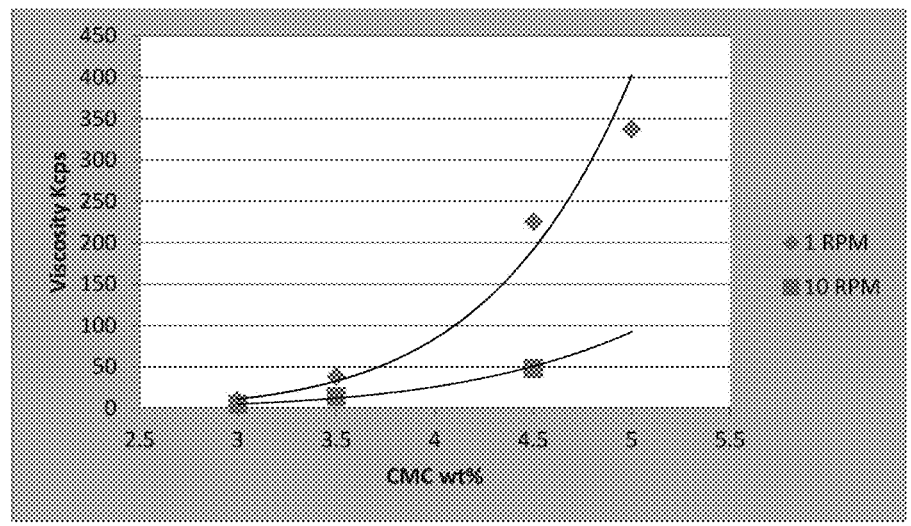
FIG. 1 is a graph of the viscosities of various gels.

The present invention relates to a flowable composition that adheres to wet tissue, and methods of making and using the composition. The composition provides a number of benefits, including the ability to provide a reduction in surgical adhesion and also by serving as a sealant or filler in certain applications, such as in the lung or other tissue region. It is desired that the composition be substantially free of byproducts of human or animal origin. The composition may include an absorbable ionic gel with a powder, where the powder may include a plurality of fibers (including micro-fibers) or granules, including pre-processed fibers or materials such as freeze-dried materials. The resulting mixture has a useful viscoelastic property.

The composition includes a first component, which may be a gel, including an ionic gel. Cellulosic gels are particularly useful, including carboxymethyl cellulose (CMC). The CMC within the gel may have a molecular weight average of about 300 kDa to about 100 kDa, or about 300 kDa to about 250 kDa, or less than about 2.50 kDa. The second component to be mixed with the first component is desirably a second cellulose material, but desirably is in the form of a powder of granules or small fibers. In one mixture, this second component may include an oxidized regenerated cellulose (ORC). The first component and/or the second component may include a polysaccharide.

As used herein, a "low" or "lower" molecular weight refers to a composition having an average molecular weight of about 90 kDa or less. The term "medium" molecular weight refers to a composition having an average molecular weight of about 300 kDa to about 100 or 90 kDa. The term "high" or "higher" molecular weight refers to a composition having a molecular weight of about 300 to about 700 kDa. The use of a first component having an average molecular weight of about 250 kDa or less (e.g., a medium molecular weight) is beneficial, as materials having a molecular weight average of about 2.50 KDa or less are easier for the body to eliminate. The molecular weight average refers to the molecular weight prior to steam sterilization, as steam sterilization may affect the average molecular weight of the product.

Higher molecular weight materials, such as CMC gels, may provide beneficial results, but have difficulty being eliminated by the body. Thus, it is a goal of the present invention to provide a lower molecular weight CMC gel. It is envisioned that combining low molecular weight CMC with higher amounts of ORC may also be suitable for the various uses described herein. It has been found that the mixing of the first gel component with a second component in the form of micro fibers allows the use of a lower molecular weight hydro gel and still maintains adhesion prevention, thus providing properties of a higher molecular weight gel without needing such high molecular weights. It has been found that using the first component with this medium molecular weight provides an equally efficacious composition as a higher molecular weight material, when it is mixed with the aforementioned micro fibers. The ORC fibers, when mixed with the CMC gel, form a material having entangled fibers or longer range ionic interaction which, in addition to the adhesion prevention properties of the CMC gel, create an improved physical barrier between the tissue layers prior to absorption. The entangled fibers are suspended in the gel and have third dimension of depth as an improved adhesion prevention barrier. It may be further desired that the mixture includes a biocompatible liquid material, such as water or saline.

Since CMC dissolves, but does not degrade in the body, it is desired that the final applied composition include CMC in a low concentration and with the aforementioned medium or lower molecular weight. The first component (the CMC gel) may include CMC in an amount of about 1% to about 10% by weight of the gel, or from about 3% to about 6% by weight of the gel, and may include CMC in an amount of about 4.5% by weight of the gel. The CMC gel may be prepared by mixing CMC, such as CMC particles, with water or other aqueous liquid to form a gel. The gel could be used soon after sterilization, if desired, however the gel should desirably be allowed to rest for a short period of time after sterilization, such as about 7 days to about 14 days, so as to allow the viscosity of the gel to increase and become more stable. If desired, however, the CMC gel may be stored for a significantly longer period of time, including up to 1 year, up to two years, or up to five years. In some aspects, it may be desired that an additional salt component, such as $CaCl_2$, be added to the CMC gel.

Covalent absorbable hydrogels often create some potential biocompatibility issue since a reactive component is introduced in the human body without guaranty that the chemical crosslinking reaction will be complete, leaving reactive species in-situ. Ionic gels represent a difficult balance between ease of expression, the ability to stay in place with good cohesive properties and the ability to adhere to wet surfaces. The present composition may include, or may consist of, a hydrocolloid gel of carboxymethyl cellulose having an average molecular weight less than or equal to about 250 kDa or about 100 to about 300 kDa, mixed with saline or water and oxidized regenerated cellulose in the form of a powder of granules or micro-fibers.

The second component, which is a dry component in the form of a powder, may be in the form of fibers or granules (as used herein, a "powder" refers to a dry composition that includes particles in the form of micro-fibers, fibers, or granules, including pre-processed fibers or materials such as freeze-dried materials). The micro-fibers may have an average aspect ratio (fiber length to diameter) of about 1 to about 50, or about 2 to about 40, or about 3 to about 30, or about 4 to about 20, or about 5 to about 10. Preferably, the aspect ratio (fiber length to diameter) is about 2 to about 5, and more preferably about 4 to about 5. As the fiber reaches a 1:1 diameter to length ratio, it becomes more like a fine powder, and when used a fine powder appears to create a more fluid (or less viscous) composite product as compared to a combination containing fibers having a greater aspect ratio. A fine powder may be difficult to mix with the gel, since the powder becomes compacted. As the fiber ratio gets greater (more elongated), the fibers sometime become difficult to mix, but they tend to make the resulting composite product more viscous due to the entanglement of the fibers or longer range ionic bonding with the gel. The desired composite material, for application of lung volume reduction or for adhesion prevention, desirably has a suitable viscosity, which may be provided by the aspect ratio of about 2 to about 5, as noted above.

For example, the fibers may have a diameter average of about 20 μm to about 50 μm and a length average of about 60 to about 250 μm, more desirably the diameter average is about 20 to about 30 μm and the length average is about 80 to about 120 μm. Smaller or larger diameters and lengths may be used, but the overall surface of the particles should remain small. This aspect ratio provides a suitable size for wetting and mixing, while avoiding issues such as clotting or clumping, which can impact delivery as well as adhesion and biological effect. However, smaller fibers may have a tendency to absorb faster and therefore have an increased local acidity as compared to larger (longer) fibers. Therefore, it may be desired to have fibers that are not so small as to have an increased local acidity, but not too long so as to cause difficulty in mixing and application.

The powdered second component may include microfibers or granules that create a local acidity around the microfibers or granules. This local acidity may have a pH of less than or about 6, or from about 1 to about 4.5, or about 2.5 to about 3.5. This local acidity allows a gel composition to retain its barrier effect for a longer time before being absorbed by the body. The desired time for the barrier effect to remain before absorption is about 7 to about 14, and more desirably about 10 days, and preferably is absorbed by the body within about 50 days or less than 40 days. Of course, depending upon the location of placement within the body, the overall absorption time may be increased or decreased. The gel compositions should have a sufficient viscosity, yet remain flowable, so that they may be placed in the desired location, while being delivered through small openings or trocars, and may be delivered accurately through surgical procedures such as laparoscopic procedures. The material adheres to wet tissue, so that it will remain in place for a sufficient length of time.

Microfibers of the cellulose, such as ORC, may be prepared by any method, such as chopping, ball milling or grinding, or may include post-processed material such as that prepared by lyophilization. The ORC powder may be acidic, having a pH of about 6 to about 1, or about 4.5 to about 2.5, or about 3 to about 2. The second component may be present in about 1 gram.

It would be helpful if the three components are mixed with each other at the time of use or at some point in time near the desired time of use, for example, less than one hour prior to use, or less than thirty minutes prior to use. The composition allows mixing of hydro gels and highly hydrophilic micro-solids without gel blocking, thereby improving shelf life and processing issues. If the composition is premixed and stored for an extended period of time (e.g., longer than one day), the ORC will start degrading and thereby complicate shelf life and efficacy.

The mixing of the components can be accomplished by transfer from standard luerlock syringe to syringe for small volumes (10 mL or less than about 10 mL depending on viscosity, fiber, and composite material volumes) or with a more ergonomic, reliable mixing apparatus syringe, such as that disclosed in Applicant's co-pending patent application entitled "Mixing and dispensing apparatus for combination materials", U.S. Patent Application No. 62/026,131, filed Jul. 18, 2014, the entire content of which is incorporated by reference herein. The composition may be mixed in an apparatus which is capable of serving both as a mixer and also as a dispenser. It is useful to mix the composition soon before application or delivery of the composition, such as within one minute after mixing is complete to about 30 minutes after mixing is complete, and most desirably within about 5 minutes after mixing is complete. Dispensing may be achieved through delivery through a tube or other delivery system, where the delivery system may include a balloon catheter for delivery.

The final composition may include the three components component, second component, water or saline) in any desired amounts. Alternatively, the final composition may include the aforementioned three components with an additional salt component in any desired amount. The first component, which may include a CMC gel, may be present in an amount of from about 1 ml to about 10 ml, while the second component, which may be a powder ORC, may be present in an amount of about 0.1 gram to about 2 grams, more specifically about 0.5 grams to about 1 gram, while the water or saline may be present in an amount of from about 0.01 ml to about 4 ml. These amounts may be increased or decreased, while maintaining the relative ratios of the components. The amount of aqueous material is related to the amount of powder material and gel used, where the aqueous material is present in an amount of about 0.1 to about 4 times the amount of powder. Thus, if 1 gram of ORC powder is used, there is about 0.1 to about 4 mL of aqueous material. If more gel material is used, less aqueous material may be required, due to the liquid nature of the gel. It is noted that, in some instances, the water content of the gel component may be sufficiently high that additional water is not necessary, and therefore the composition may only include a gel with sufficiently high water content and a second component, such as a powder ORC. In addition, if less powder is used, less aqueous material may be required. The aqueous material aids in mixing the powder with the gel, and therefore, if less powder material is present, less aqueous material may be required. In addition, if an efficient mixing device is used, the aqueous phase may not be required at all.

The amounts listed above are suitable for about 1 gram of the second component (the powder), and may be modified to maintain an equivalent ratio if more or less powder is used. For example, if a larger mixing apparatus is used, greater amounts of materials may be used, and vice versa. For example, if two grams of ORC powder are used, then the first component (the gel) may be present from about 2 mL to about 20 mL, and the third component (aqueous material) may be present in amounts from about 0.2 mL to about 8 mL. The first component (i.e., the cellulose gel) may be present in an amount of about 25-80 weight percent of the final composite material, and the second component (i.e., the powder) may be present in an amount of from about 0.1 to about 25 weight percent of the final composite material.

If used, an additional salt may be present in an amount less than the second component but such that the osmolality of the final gel composition remains at a level that is suitable for human implantation (for example, about 300 mOsm/L). The additional salt is useful for providing a suitable viscosity, and also for balancing the ionic concentration of the human body (osmotic pressure). If included, an optional salt may be present in an amount of about 0.5 to about 1.0 percent by weight of the first component and may be included as part of the first component.

The present resulting composite mixture is gel-like in form, is flowable, and has a unique viscoelastic and handling property allows ease of delivery and turns into a stable absorbable filler barrier after delivery. The resulting composite gel product is useful as a biomedical material, as it provides suitable biomedical properties while allowing for easier elimination by the body due to the medium to lower molecular weight products used. Delivery may be to a target site, such as a surgical site or wound. It may be desired that the mixed composition be opaque or have some degree of color, so that it can be easily visualized during application of the material. Further, the final composition may be bactericidal, such that it will prohibit the growth of bacteria at the site of implantation, even in contaminated fields. The composite material may have one or more additives that are capable of being displayed or detected under fluoroscopy or other similar visual methods.

Method of Preparing a Composite Mixture

The present invention provides a method of preparing a composite mixture. The method described herein will refer to the first component as CMC gel, and the second component as ORC powder. The method includes the first step of preparing a gel from CMC, which may include water, saline, or other aqueous material, and may include a separate salt, such as CaCl$_2$. It is helpful if this CMC gel is prepared in advance of the preparation of the composition to ensure stabilization of viscosity, such as at least one week or at least two weeks prior to the mixing with the powdered material. The pre-made CMC gel may be stored until ready for use.

When the final composition is ready to be prepared, the ORC powder may be provided to a user, and the powder may be formed into a suspension by mixing the powder with water or saline, or other aqueous liquid material. After the suspension is formed, the suspension may be combined with the CMC gel, and the components mixed with each other. Mixing may be achieved by hand, or with a suitable mixing apparatus, or via syringe mixing. In some embodiments, the mixing is achieved by a mixing apparatus inserted into a syringe, which adequately mixes the composition without the need for high-shear electric mixers. The mixing is performed until a substantially uniform gel is formed, and may be completed with about 20 strokes or less. While some solids may be visual in the final mixed composition, it is desired that the resulting gel composite be substantially uniformly mixed and any solids present in the final gel be dispersed throughout the gel composition.

The resulting composition should be applied to a target area or target site within about one hour after mixing is complete, or within about 30 minutes after mixing is complete, but most desirably within about 5 minutes or within about 1 minute after mixing is complete. In some aspects, the final mixed product may be applied as soon as mixing is complete. It has been found that if the mixed composition is allowed to sit for twenty minutes after mixing is complete, the viscosity increases and the composition becomes more difficult to expel from the delivery device. Although the composition may be allowed to rest for up to thirty minutes after mixing, it is preferred to expel the composition from zero minutes to about 5 minutes after mixing is complete. If a lower viscosity is required for delivery, the mixed composition can be quickly remixed (sheared) to lower the viscosity. The resulting composition may be dispensed or expressed from a syringe or other delivery system and adhered to a desired surface. The surface may be a wet surface. Delivery or expression may be achieved through a needle, cannula, elongated tube, or other means, and the delivery may be sprayed, such as with a gas-assisted spray device, if desired.

The combination of the first component (for example, a CMC gel having a medium average molecular weight), the second component (for example, an ORC micro-fiber powder), and an aqueous material (for example, water or saline), and optionally with an added salt provides a suitable product with desired viscosity and adherence properties, particularly when the water or saline is first mixed with the powder, and then the resulting suspension added to the gel material. The resulting composite gel remains in the body for a suitable period of time, such as about 7-14 days, or about 10 days, and preferably within about 30-45 days or less than 30 days, when it breaks down and be absorbed or eliminated by the body.

It has been found that a combination of CMC gel with ORC micro-fiber powder in the absence of water or other aqueous liquid may provide gel blocking, as the gel tends to encapsulate the powder, rendering the various components difficult to mix uniformly. Further, to achieve even suitable mixing, in the absence of water or other aqueous liquid (such as saline), the result was that mixing in a syringe was difficult. Mixing in the absence of water, saline or other aqueous liquid was found to require additional mixing means, such as a high shear mixer, which is not practical in certain settings, such as in an operating or emergency room. It has also been found that if CMC gel is first mixed with water or saline or other aqueous liquid, and then ORC micro-fiber powder added, the result was similar difficulties with uniform mixing. The powder was found to be encapsulated by the gel/water mixture. Similarly, the combination of CMC gel mixed with ORC powder, followed by addition of water or saline or other aqueous liquid also provided difficulty in mixing appropriately. Therefore, it is desired to add water or saline or other aqueous liquid to the powder first, and then add the resulting suspension to the gel component. Further, if water or aqueous liquid is added, similar or equivalent amounts of water (or other aqueous component) may be removed from the CMC gel so as to not further lower the desired viscosity of the resulting combination.

The resulting combination material is desirably formed with water or saline as the aqueous liquid material, it has been found that creating a suspension of the powder with a non-aqueous liquid, such as glycerol, low molecular weight PEG or low molecular weight PEO, provides adequate mixing but did not provide sufficient adherence to a wet surface.

A composite material and method of making and using this composite material are provided. The composite material includes a combination of: a first component, which may be a gel, and may be a CMC gel; a second component, which may be a powder, and may be an ORC powder, where the ORC is in the form of micro-fibers; a third component, which may be an aqueous material such as water or saline. The composite material may include an additional salt, such as CaCl$_2$. The CMC gel includes CMC in an amount of from about 1-10% by weight of the gel (desirably about 3-6% by weight of the gel), and the CMC may have either a medium average molecular weight (from about 90 to about 300 kDa) or a lower average molecular weight (about 90 kDa or lower). The ORC, if in the form of micro-fibers, desirably has a length to diameter aspect ratio of about 4-5.

A method is provided, where the second component is prepared into a suspension by mixing with the aqueous material, and the suspension is then mixed with the first component to provide a substantially uniform composite material. The additional salt, if used, may be mixed with the first component prior to adding the suspension, or may be added concurrently with or after adding the suspension. The CMC gel may be prepared by mixing CMC particles with water or other aqueous material, and allowing the CMC particles to swell and form a gel prior to use. The formation of the CMC gel may be prepared and stored at ambient temperature at least one day prior to formation of the composite material, or at least one week, or at least two weeks prior to formation of the composite material once sterilized.

The resulting composite material may be used in bodily applications, such as for prevention or reduction in surgical adhesions, for example. The resulting composite material may be applied by a user to the target site through a syringe or through any desired application device. The composite material may be shear-thinned prior to application to the target site. The resulting composite material may be at least partially resorbable by the body into which it is applied, or it may be capable of being broken down by the body and excreted by the body. The composite material may remain in place where applied in the body for about 7 to about 14 days, or about 10 days, or about 30 days and preferably within 60 days, when used internally. However, if the composition is used in the airways of a lung, such as during lung volume reduction treatment, or if the composition is used for drug delivery, the composite material may have a residence time that is longer than 10 days, or longer than 30 days, and may be up to 60 days.

There may be provided a kit for preparing a biomedical composition, including a first container including a gel of CMC and an aqueous material, and a second container containing ORC particles or micro-fibers. A kit may include a third container including an aqueous material, such as water or saline. The kit may include a fourth container, which includes a device in which the composite material can be mixed and/or expressed, such as a syringe.

The components may be sterilized through the same or through different methods prior to being provided in a kit. For example, CMC gel may be sterilized through heat or steam sterilization, while ORC powder may be sterilized through radiation treatment.

Use of a Composite Mixture

The resulting composite material is gel-like, and has a suitable viscosity. It is thoroughly mixed, such that the solid component(s) are fairly uniformly dispersed throughout the final composite material. It is understood that complete uniformity is not required, but substantial uniformity is desired. The composite material may be capable of being delivered through the application of a syringe, which may have a plunger that is pushed, levered or twisted to advance the piston. The composite material may be delivered to any desired target site, through the use of a dispenser tip, or may use an elongated tube or cannula to deliver the composite material. The composite material may be delivered via gas-assisted means, or sprayed onto the desired site, if desired.

For example, the gel may be dispensed through tubes between 0.5 cm to 200 cm in length but could range from 25 cm to 150 cm or 50 cm to 100 cm depending on the surgical need. Further, the composite material may be dispensed through long or short tubes having an inner diameter as small as 0.1 mm to 10 mm or between 0.5 mm to 5 mm, or from 1 mm to 3 mm, with a delivery tube wall thickness that could range from 0.025 mm to 1 mm depending on the surgical need. Delivery may be achieved with a balloon catheter.

The target site may be any desired site, and the material is suitably useful in biomedical procedures, such as to act as a barrier to reduce the presence of adhesions in a surgical site. The composite material is flow/able upon delivery, but then remains in its state for an extended period of time post-delivery, such as about 7 days, about 10 days, or about 14 days, or about 30 days, but preferably is absorbed by the body within about 60 days or less than 60 days.

The present composite material may be used for a number of various purposes, including, for example, as a carrier for general surgical purposes. Given the viscosity levels of the resulting gel, and the ability of the inventive composition to suitably adhere within a body region for a set period of time, before it is broken down within the body and excreted by the body, the uses for the inventive composition are numerous. In addition, the present composite gel material has excellent tissue adherence properties, in particular the ability to stick to wet tissue or surfaces. The combination of viscosity and tissue adherence properties makes this composite material well suited to stay where placed after surgical intervention.

In addition to use as a carrier for general surgical purposes, as mentioned above, it can be used in open or minimally invasive surgical procedures to limit or eliminate adhesions formation (adhesion formation being defined as preventing two tissue walls or areas from becoming attached to each other). Any desired material, including drug or other biological material can be carried in the inventive composite material and delivered to the target site. The composite material may be used to deliver drug or radiation within the composite matrix in a surgical setting. Similarly, the composite gel material may be useful to keep drug or radiation delivered substances where placed post delivered by acting as an absorbable plug within the lung or any surgical site. The ability to remain in the delivered site for an extended period of time (e.g., at least 7 days, at least 14 days, or less than 30 days) allows the composite material to be a suitable drug or radiation delivery vehicle.

The composite gel material may be useful in various viscosities to limit or eliminate pneumothorax either through interventional or open surgical means. Additionally, the gel may be used to seal or plug or minimize fluid leakage after surgical intervention alone or in combination with being a sealant and adhesion preventative barrier.

In an additional aspect, the composite material may be used to address lung infections whereas a version of the gel (including ORC gel and CMC powder) in various viscosities and/or acidity levels may be used to control bacterial growth and or contain a drug to limit, control or cure lung infections. The composite gel may be useful as a temporary filler or to deliver a permanent filler material to reduce the risk of hematoma, or to separate adjacent surfaces with a lubricating material.

The composite material may further include an anti-bacterial material, or the material may simply have a pH capable of acting as an anti-bacterial material (such as a low pH, e.g., at 3 or lower). In this case, the composite material may therefore be used to control or limit bacterial growth on a surgical site. It may be desired that the composite material for any of the above uses include an anti-bacterial agent so as to provide the additional purpose of limiting bacterial growth. In addition, regardless of the use, the composite material may include one or more imaging agents in the formulation. For example, the material may include radiopaque agents like barium or other material. The composite material may include other agents that enhance MRI or ultrasound imaging. These imaging agents aid the clinician in dispensing the composite material in the proper location, particularly if the location is internal and hidden from view by eyesight alone.

It may be desired to mix the components in such a fashion that the resulting material has a foamed element to it, or where the end result is a foam material. Foaming may allow less material to be put in (on a mass basis). In addition, using a foamed material may also help in ultrasound or MRI imaging.

The composite material described above may be used in any of the above procedures and for the above purposes, and may include various combinations of the elements described above. For example, the composite material may be intended to be used as a barrier to prevent adhesions, and may include anti-bacterial agents and/or an imaging agent. In other aspects, the composite material may be used within the lung, to be delivered by an elongated tube within the lung, and may include an imaging agent to aid in visualizing the delivery. Additionally the composite material may be used in combination with other implantable mechanical devices such as a valve or plug or filter as examples.

EXAMPLES

The present invention will be better understood through the explanation of several examples and tests conducted.

The following examples are not intended to be limiting but rather aid in explaining and understanding the invention.

Example 1

CMC Gel Composition

A hydrocolloid gel formulation was developed to obtain sufficient adhesion reduction results, while using a lower molecular weight and weight percent of CMC. The intent of this composition is to provide a suitable safety profile for biocompatibility. A useful medium-molecular weight CMC gel formulation is as follows in Table 1:

TABLE 1

CMC Gel

| Component | Wt % |
|---|---|
| $H_2O$ | 95.15 |
| CMC (Medium Mw = 250 KDa, 0.81 substitution - carboxymethyl group substituted for hydrogen) | 4.28 |
| $CaCl_2$ | 0.57 |

The gel of Table 1 was used in a rabbit side wall model, and it was found that the efficacy of the gel was not related to the CMC concentration. It is noted that the tests were between 3 and 6 weight percent of CMC, but that efficacy was sensitive to molecular weight, it was found that higher molecular weight CMC gels show less adhesion. The $CaCl_2$ salt was added to increase gel viscosity and balance the osmolality of the final composite gel to around 300 mOsm. CMC gel may be sterilized by steam heat.

Example 2

CMC Only Gel

Three CMC gel compositions were tested, where the CMC used had a molecular weight average of about 250 kDa, with a 0.7 substitution. The concentration of CMC in the solution strongly influence the viscosity of the gel as can be seen in FIG. 1 showing the measured 1.5 viscosity of the CMC gel as a function of the CMC concentration and viscometer rotating speed. For the molecular weight chosen (250 kDa), a large increase in viscosity is observed between 3 and 6% CMC concentration.

To further illustrate the effect of CMC concentration in the gel, the same gel was prepared at concentration of 3, 4.5 and 6% of CMC (See FIG. 2). In this example, sample #25 was a gel including about 3% CMC. Sample #26 was a gel including about 4.5% CMC, and sample #27 was a gel including about 6% CMC. Screening Concentration Post autoclave, 1 week relaxed.

Figures 2A, 2B, 2C:
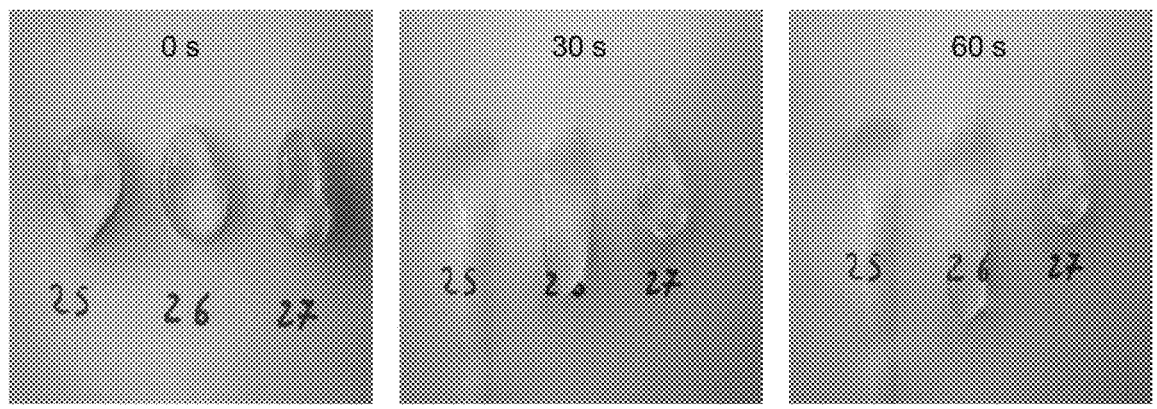
FIGS. 2A-2C show samples of gels taken at various times.

Blobs of the three CMC samples were placed onto a paper and inverted at 90 degrees (vertical). They were measured after three time periods, zero seconds, thirty seconds and sixty seconds. Pictures of the gels were taken, and are provided as FIGS. 2A, 2B and 2C. FIG. 2A shows the three gels after initial application (at T=0). FIG. 2B shows the three gels after thirty seconds, and FIG. 2C shows the three gels after sixty seconds. As can be seen, the highest concentration of CMC in the gel (sample #27) had the highest viscosity and least run-off after the extended period of time. The lowest concentration of CMC in the gel (sample #25) was least viscous and ran off earliest and most.

Example 3

Preparation of a Composite Gel Composition a) ORC Microfibers

ORC microfibers were obtained from ball milling Interceed™ fabric (Ethicon) to a fiber size aspect ratio from 4 to 5, with an average fiber size aspect ratio of about 4.75 (S.D. of 3.35). The fibers measured had a diameter average of 20.99 (S.D. 7.84 μm) and a length average of 95.34 μm (S.D. 63.84 μm). This measurement was obtained by averaging 100 random fibers in the sample. In another method of measuring the aspect ratio, three groups of ten samples were acquired, and the small/medium/large fibers lengths were measured, which resulted in a measured median length of 118.9 μm. Thus, the average fiber length in the study was from 95.34 μm to 118.9 μm, depending upon the random fiber selection. This aspect ratio provided easiest mixing of the composite gel, while also allowing expression of composite gels through micro size needles and tubes. The ORC microfibers were sterilized by gamma radiation.

In a larger aspect ratio, the ORC forming was unstable or inconsistent, while a lower aspect ratio was not desirable due to the requirement of longer ball milling times, which might result in thermal or other damage to the fibers, including possible contamination from ball material. It is contemplated that other methods of sizing the fibers may be useful in the preparation. In subsequent animal studies using ORC microfibers having a diameter average of 20 μm and average length of 30-40 μm (prepared from Surgicel™), it was found that due to the increased oxidation levels used in processing this ORC material, and/or the smaller aspect ratio of the resulting fibers, degradation or absorption occurred faster than with the ORC fibers (formed from Interceed™ fabric) having an aspect ratio of 4 to 5. In addition, in animal studies, there was evidence of animal pneumonia and high tissue reaction when using the ORC fibers having a diameter average of 20 μm and average length of 30-40 μm. Therefore, the fiber aspect ratio, the materials used, or the materials oxidizing during process may each play a role in the efficacy of the mixed composition, particularly in a lung application. This may be due to either the quick release of acids as the material absorbs or the reduced time period the material remains present.

b) Mixing of the Composite Gel and Final Composition

The desired composition of the final product is obtained by mixing a CMC gel, saline solution and ORC microfibers. The composition included about 8 ml of CMC gel from composition listed in Table 1 (Mw=250 KDa, 0.81 substitution, 4.28% CMC), about 2 ml of saline, and about 1 gram of ORC fibers. The ORC fibers were prepared by ball milling Interceed™ fabric (Ethicon), and the average aspect ratio was around 5 for a fiber diameter of 20 microns. The composite gel was obtained by first creating a suspension of the ORC fibers with the saline, and then mixing with the CMC gel. The final composition of the mixed composite gel was set forth in Table 2:

TABLE 2

Final composition of the composite gel

| | $H_2O$ | CMC | $CaCl_2$ | NaCl | ORC powder |
|---|---|---|---|---|---|
| Composition wt % | 87.24% | 3.11% | 0.41% | 0.16% | 9.08% |

Figures 3A, 3B:
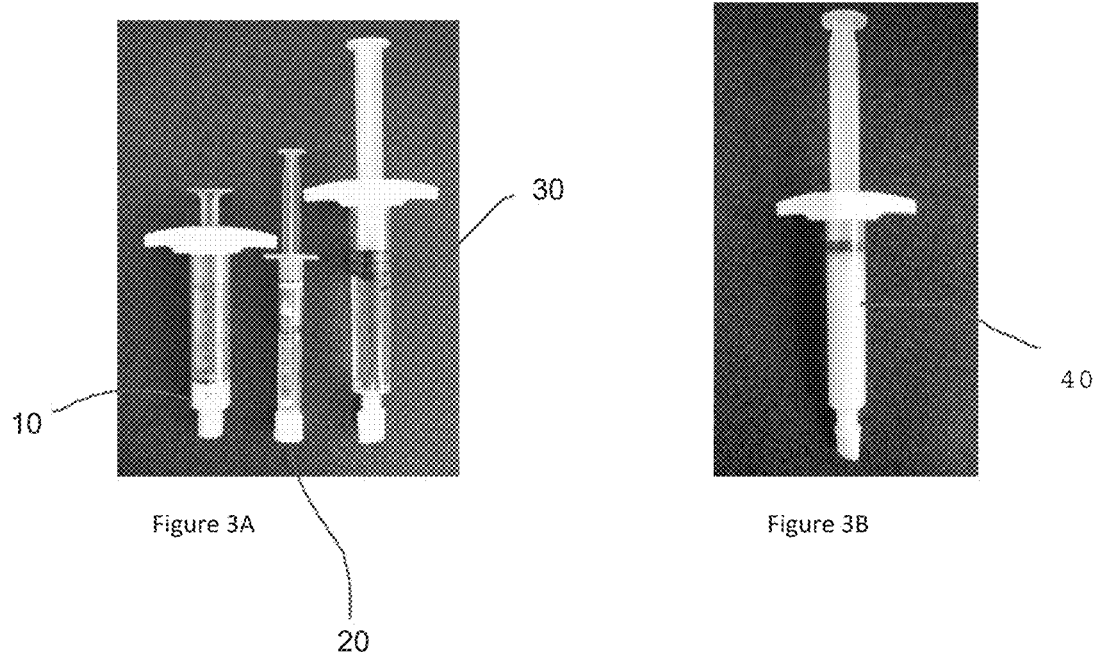
FIG. 3A shows a kit providing various components prior to mixing.
FIG. 3B shows the kit after mixing.

The $CaCl_2$ was found to improve the gelling of the composition, and therefore was useful but is not essential. A picture of the components prior to mixing (syringe to syringe), such as would be provided by a kit including the components, is seen in FIG. 3A, and after mixing is seen in FIG. 3B. A kit may include a first container including a gel of CMC and an aqueous material 30, and a second container containing ORC particles or micro-fibers 10. A kit may include a third container including an aqueous material, such as water or saline 20. The kit may include a fourth container, which includes a device in which the composite material can be mixed and/or expressed, such as a syringe. The components may be sterilized prior to being provided in a kit.

As can be seen in FIG. 3B, a syringe may be used to contain the resulting mixed composite product 40 regardless of the mixing method used.

Example 4

Testing of Composite Gel

The composite gel of Example 3 was prepared as described, and was tested in cadaver labs and rated by surgeons. The surgeons rated the composite gel of Example 3 as performing very well in terms of mixing and handling properties, specifically gel expressibility and gel staying in place on the tissue. In the test, 0.5 ml of the composite gel and comparative samples, including CMC alone and Intercoat alone (Intercoat is a high molecular weight CMC gel mixed with PEO and salt for osmolitic balance) were applied on corium (bovine collagen substrate) and for 3 min immersed in saline at 37 C.

Figure 4:
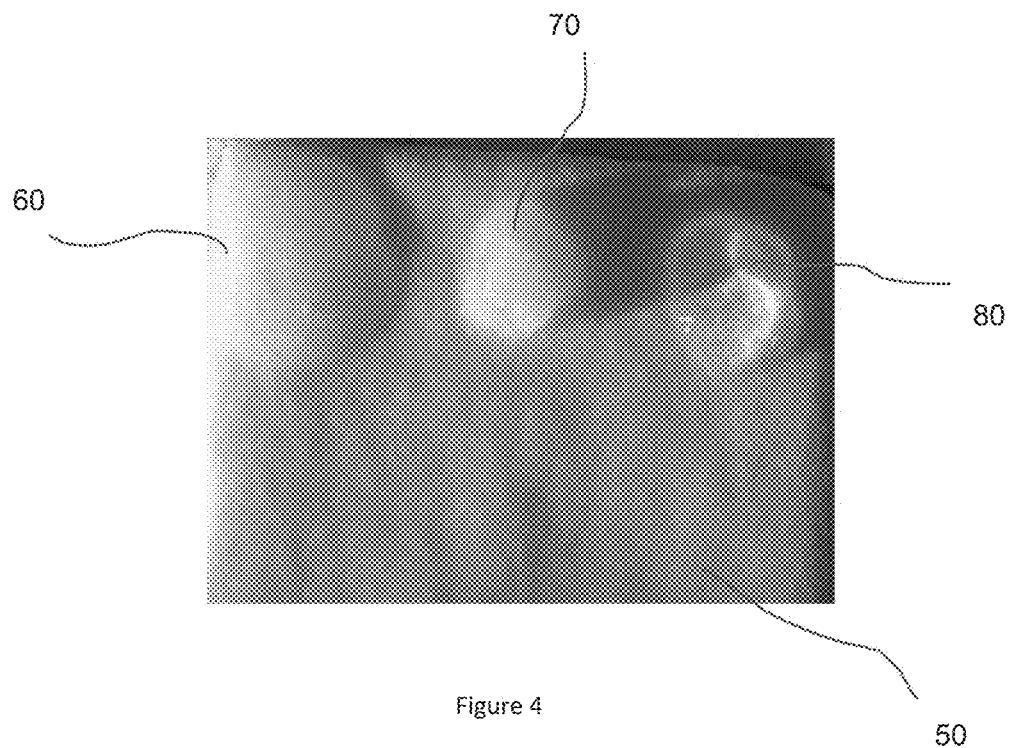
FIG. 4 shows samples of Example 4 on a wet collagen (bovine) substrate.
Figure 5:
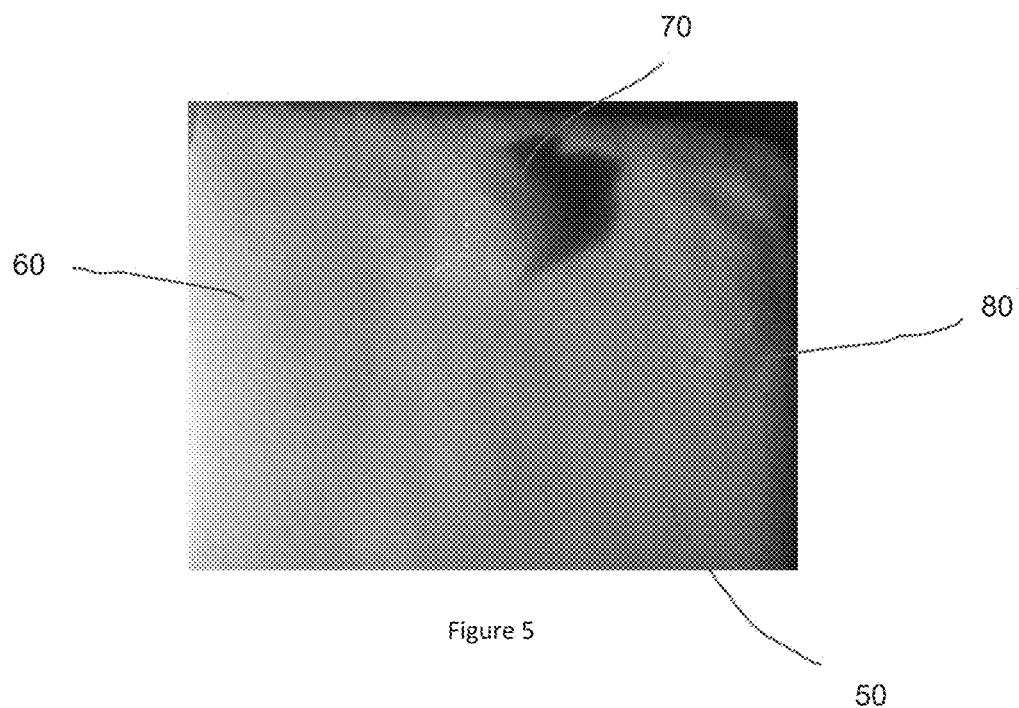
FIG. 5 shows the samples of FIG. 4 after three minute immersion into saline.
Figure 6:
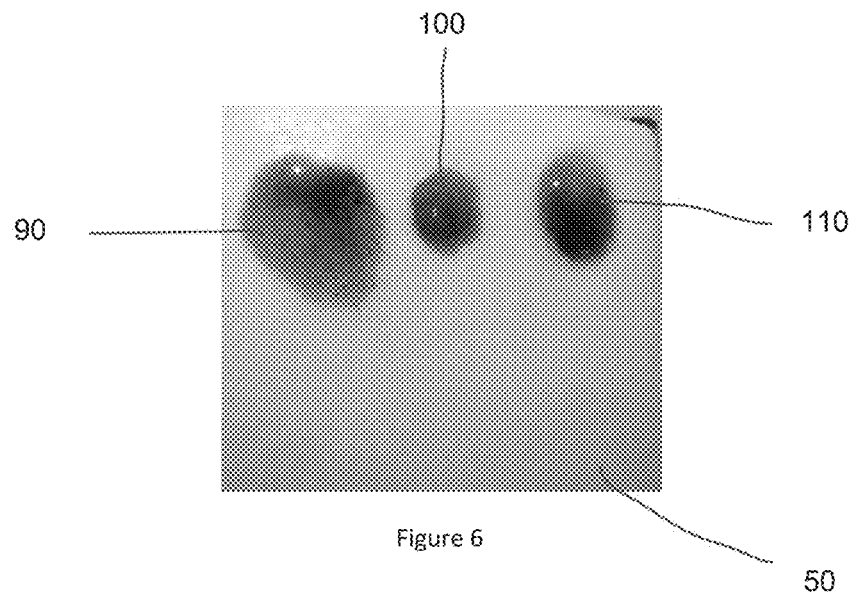
FIG. 6 shows the samples of FIG. 4 with pigment.
Figure 7:
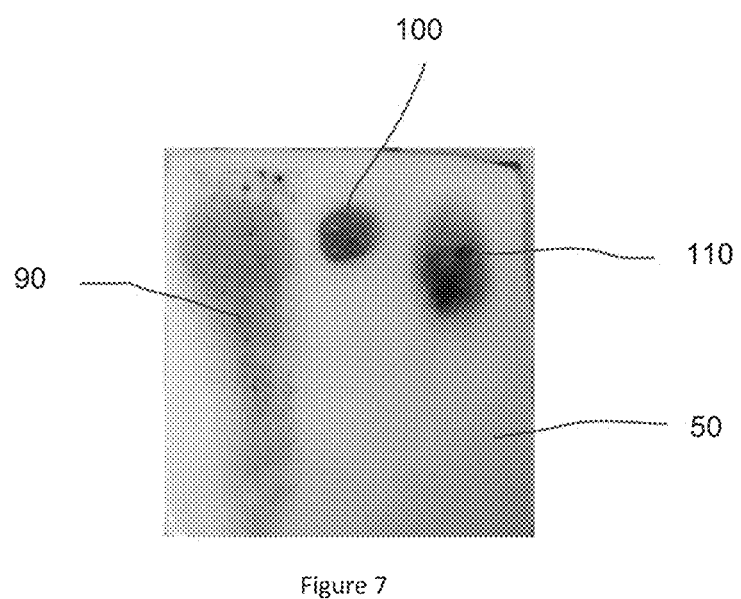
FIG. 7 shows the samples of FIG. 5 with pigment.

The results indicate that only the inventive gel remained on the tissue. FIG. 4 shows the three samples as first placed on the bovine substrate 50, with the CMC alone being farthest left (60), inventive composition being in the middle (70), and Intercoat being on the right (80). FIG. 5 shows the three samples after three minute immersion into saline at 37 C. The results of the same test performed with pigment added (for visibility) are seen in FIGS. 6 and 7. FIG. 6 shows the three samples as first placed on the bovine substrate 50, with the CMC alone being farthest left 90, inventive composition being in the middle 100, and Intercoat being on the right 110. FIG. 7 shows the three samples after three minute immersion into saline at 37 C.

As can be seen, the pigment demonstrated rim-off for the two comparative examples. The data indicates that the inventive gel 70 (FIG. 4-5) or 100 (FIG. 6-7) demonstrates surprisingly good properties of gel staying in place on wet tissue.

Example 5

Testing of Composite Gel

Figure 11:
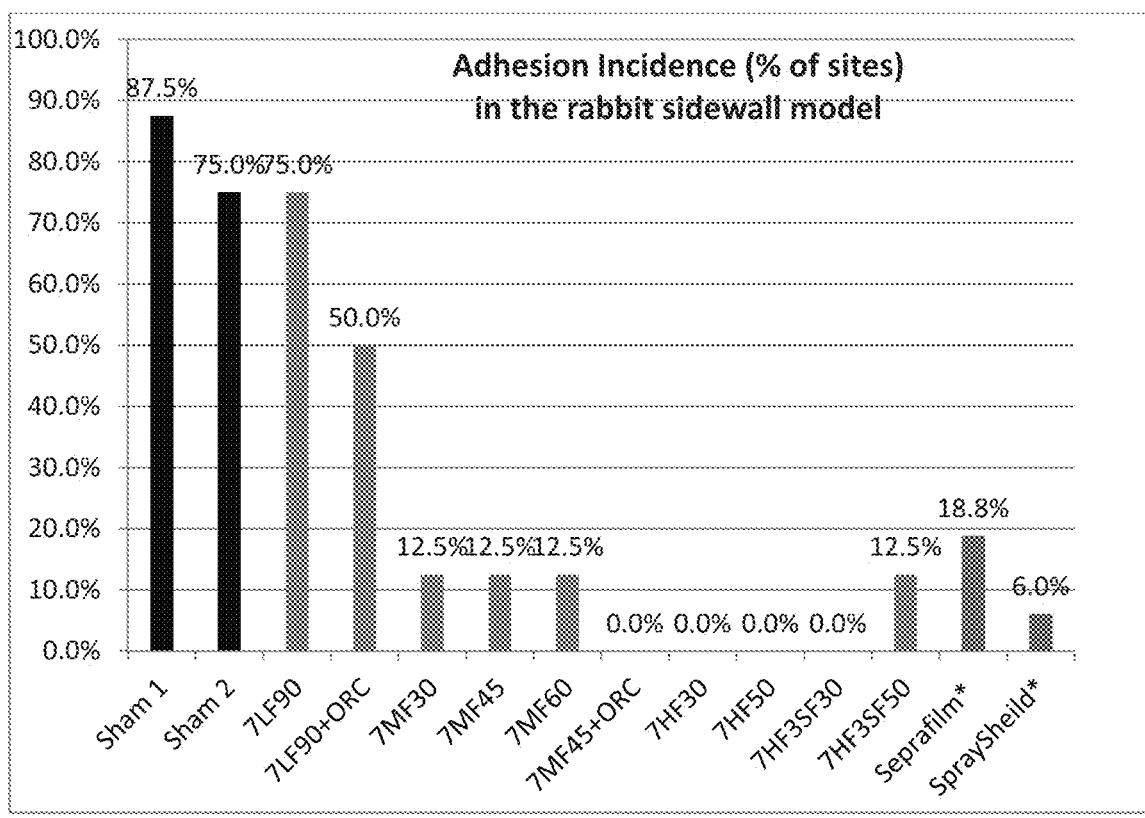
FIG. 11 shows the results of adhesion incidence.

The composite gel of Example 3 shows adhesion preventive effects in a rabbit sidewall model for adhesion prevention (adhesion rated after 2 week implantation). There was no incidence of adhesions in the 8 sites treated with the composite gel of Example 3 as defined in Table 2 and labeled 7MF45+ORC in FIG. 11, versus 75% of incidence of adhesion in the 8 controlled sites (controlled sites had no treatment, labeled as Sham 2 in FIG. 11). There were no sign of biocompatibility issues in the filtering organs.

Figure 8:
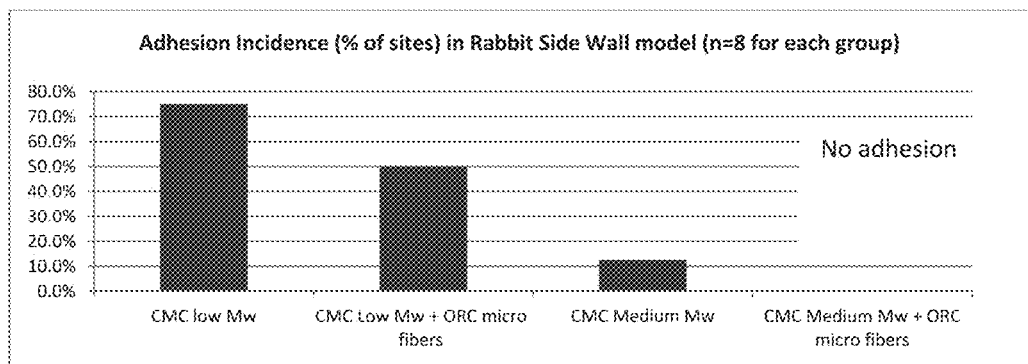
FIG. 8 shows the results of Example 5.

The beneficial effect of the ORC micro fiber suspension on the CMC gel formulation is illustrated in the chart of FIG. 8. As can be seen, the composition including ORC microfibers to a CMC gel reduces incidence of adhesion for low and medium Mw gels. The chart shows Adhesion Incidence results showing the effect of adding ORC micro fibers to gel formulations and the effect of CMC molecular weight regarding the reduction of adhesion formation.

Example 6

Physical Properties of CMC Gel

Figure 9:
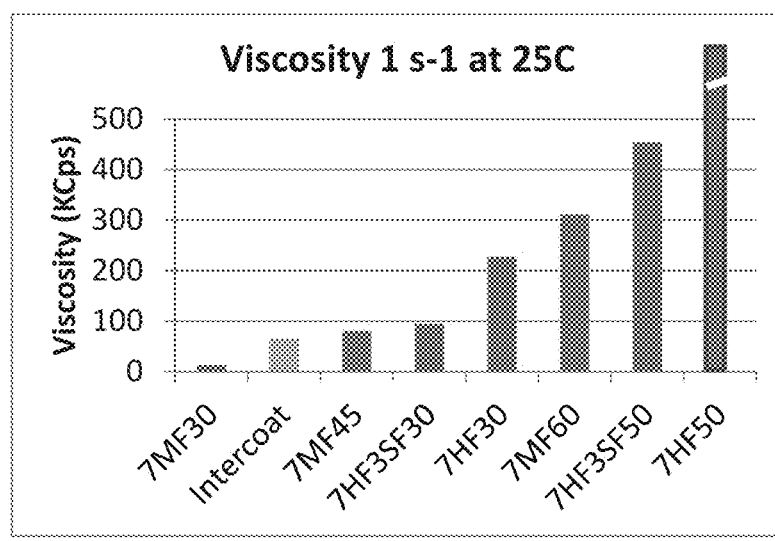
FIG. 9 shows the results of Example 6.

Various CMC gels were prepared. The compositions are set forth in the Table 3 below. These gels did not include ORC. Viscosities of these gels were measured by a rheometer, and can be seen in FIG. 9.

TABLE 3

CMC Gels

| Sample | Mw (KDAa) | Substitution | Mw (KDAa) post sterilization | Mw/Mn | CMC wt % | $CaCl_2$ wt % | Osmolality mOsm | Viscosity 1 $s^{-1}$ at 25 C. (KCps) |
|---|---|---|---|---|---|---|---|---|
| 7MF30 | 250 | 0.82 | 452 | 4.73 | 3 | 1 | 307 | 13 |
| 7MF45 | 250 | 0.82 | 438 | 4.27 | 4.5 | 0.9 | 317 | 81 |
| 7MF60 | 250 | 0.82 | 472 | 4.66 | 6 | 0.8 | 386 | 311 |
| 7MF30 | 700 | 0.84 | 1680 | 3.95 | 3 | 0.0388 | 391 | 228 |
| 7HF3SF30 | 700 | 0.92 | 1571 | 7.23 | 3 | 0.044 | 388 | 95 |
| 7HF50 | 700 | 0.84 | 1536 | 3.47 | 5 | 0.065 | 423 | Higher |
| 7HF3SF50 | 700 | 0.92 | 1407 | 5.68 | 5 | 0.0733 | 449 | 454 |
| Intercoat | | | 1038 | 7.68 | | | 300 | 65 |

Example 7

Animal Study—CMC Gel Only

Figure 10:
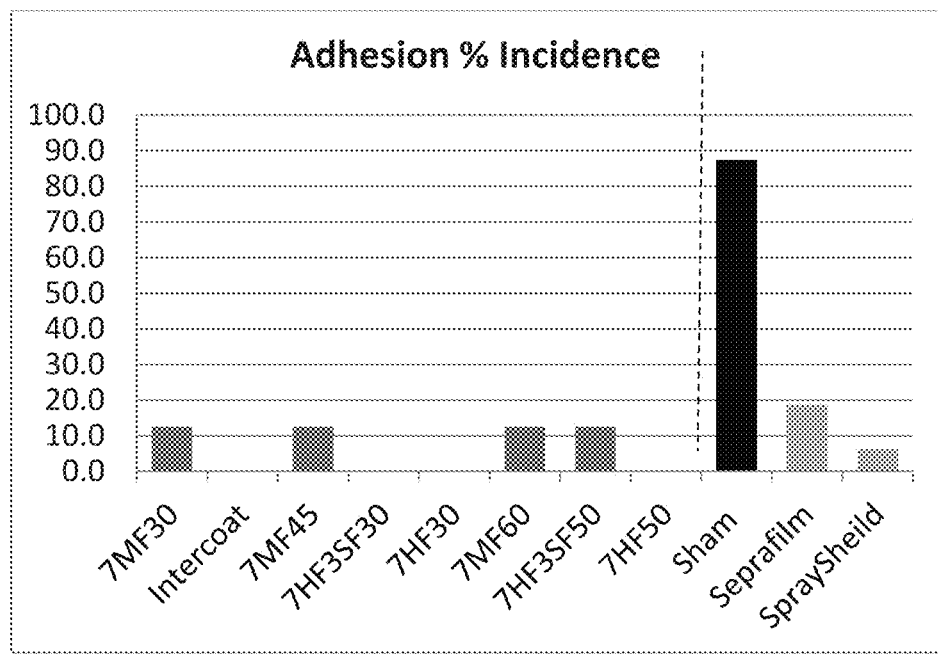
FIG. 10 shows the results of Example 7.

A study was performed on various gels containing only CMC and not ORC. The gels were applied to a rabbit side wall model. It was noted that the higher molecular weight gels performed better with respect to adhesion prevention, but higher molecular weight compositions are more difficult to remove from the body and thus lower or medium molecular weight compositions are preferred. The results are seen in the below table and in FIG. 10.

TABLE 4

CMC Gel Only Results

| Group | Sample | % Incidence of adhesion |
|---|---|---|
| Sham | no | 87.5% |
| A | 7MF30 | 12.5% |
| B | 7MF45 | 12.5% |
| C | 7MF60 | 12.5% |
| D | 7HF30 | 0% |

TABLE 4-continued

CMC Gel Only Results

| Group | Sample | % Incidence of adhesion |
|---|---|---|
| E | 7HF3SF30 | 0% |
| F | 7HF50 | 0% |
| G | 7HF3SF50 | 12.5% |

Example 8

Animal Study—Composite Gel

A second animal study was performed, where gels were applied to a rabbit side wall model as in Example 7. However, in this study, the gels applied were composite gels including the ORC powder with a medium or low molecular weight CMC gel. The below table shows the compositions. It was found that the Sample 7LF90 (gel only) showed 75% adhesion, the sample 7LF90 with ORC powder showed 50% adhesions, 7MF45 (gel only) showed 12.5% adhesions, but the Sample 7MF45 with ORC showed zero adhesions. A sham sample showed 75% adhesions. A graphical depiction of the results (along with the results of Example 7) can be seen in FIGS. 8 and 11.

As can be seen, the combination of a medium molecular weight CMC gel with ORC powder provided surprisingly beneficial results. There was a zero percent incidence of adhesion found with this composite gel. Further, there was found no histological observation of significant adverse effect on filtering organs.

TABLE 5

Results of Animal Study 2

| Sample | Mw (KDAa) | Substitution | Mw (KDAa) post sterilization | CMC wt % | ORC wt % | CaCl2 wt % | Osmolality mOsm (gel only) | Viscosity 1 s$^{-1}$ at 25 C. |
|---|---|---|---|---|---|---|---|---|
| 7LF90 | 90 (L) | 0.81 | 266 | 9 | 0 | 0.03 | 356 | 24 |
| 7LF90 + ORC | 90 (L) | 0.81 | 266 | 6.5 | 9.1 | 0.024 | 356 | na |
| 7MF45 + ORC | 250 (M) | 0.82 | 438 | 3.3 | 9.1 | 0.5 | 304 | na |

Example 9

Viscoelasticity Study—Composite Gel

Figure 12:
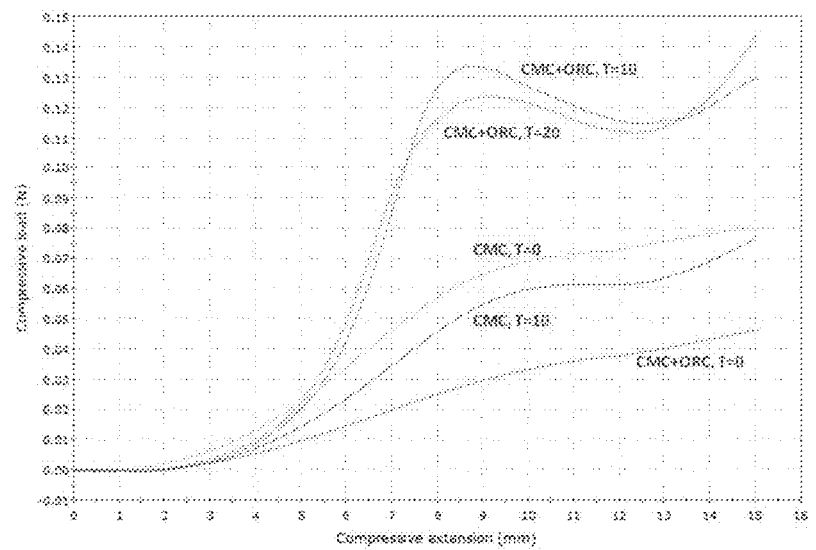
FIG. 12 shows the results of compressive extension in Example 9.

The viscoelastic properties of the composite gel (7MF45+ORC in Table 5 above) were compared to the CMC only gel (7MF45 in Table 3 from Example 6) by measuring the forces to push a 0.40 inch diameter ball into the material. This test measures the cohesiveness of the gel. The experiment was conducted just after expressing the material then repeated after a certain amount of time to demonstrate how the material relaxes and "stiffens" with time. Results are presented in FIG. 12 (T indicates the elapse time after expression from the syringe in minutes). In comparison with equal solution percentages with the gel only, the composite gel exerts less resistance to deform just after expression. This property would allow an easier spreading of the material. After 10 minutes, the composite gel is more cohesive and would stay in place better that gel only.

Figure 13:
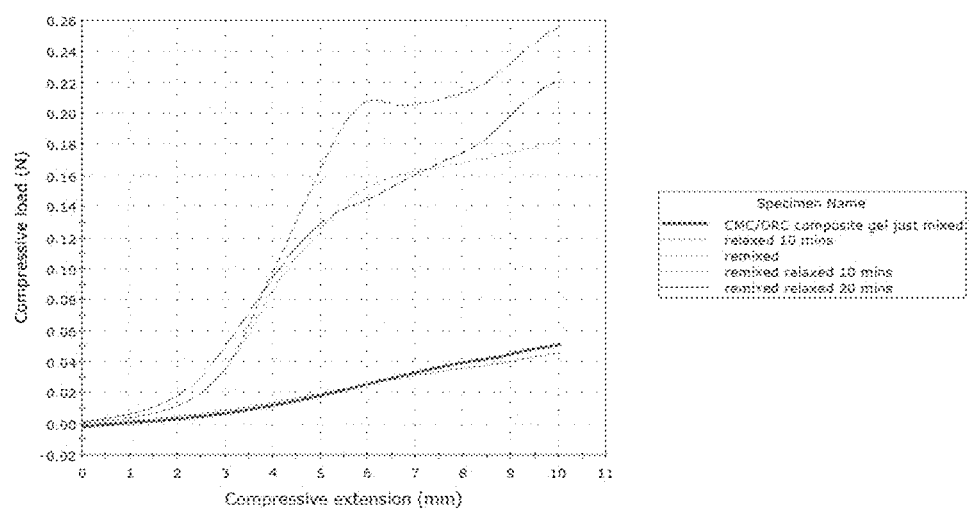
FIG. 13 shows the results of compressive extension in Example 9 after remixing.

Surprisingly, when the composite gel was remixed, the force to push the ball through the gel using the same method drops back to the initial time (see FIG. 13). Measurements were taken just after mixing, and then 10 minutes later. The same material was then remixed to demonstrate the reversibility of the shear thinning properties and return to higher cohesiveness after relaxation. Ten minutes after re-mixing, the gel appeared to return to its relaxed state with more resistance to the ball penetration. Mechanism that can explain this behavior includes considering the long range interaction provided by the fiber. Bonding appears to be weak enough to be broken by shearing the material through mixing but is recreated after relaxation.

It was found that the composite gels including CMC and URC, after 10 and 20 minutes, formed more cohesive materials that can stay in place more adequately. The resulting composite product is easy to express after mixing, then gels reversibly. This was surprising, since CMC alone does not show this property in this amplitude and ORC alone does not show this property.

Example 10

Bactericidal Properties of Composite Gel

The composite gel has bactericidal properties due to the presence of acidic ORC microfibers. Results show 99.9% efficacy on a wide spectrum of bacteria responsible for hospital infections, including MRSA 33592 (Methicillin resistant *Staphylococcus aureus*), VRE 700221, *P. aeruginosa* 9027, *S. aureus* 6538, *Acinetobacter baumannii* 15308, *Candida albicans* 10231, and *E. coli* 25922. CMC gel alone does not provide suitable bactericidal properties.

The invention claimed is:

1. A composite material comprising a mixture of:
    i. a first gel component, the first gel component comprising a carboxymethyl cellulose having a molecular weight average of about 100 to about 300 kDa, wherein the carboxymethyl cellulose is present at from about 3 to about 6 percent by weight of the first gel component;
    ii. a second powder component, the second powder component comprising a dry cellulose material, wherein the cellulose material comprises oxidized regenerated cellulose having a localized pH of from about 2.5 to about 4.5; and
    iii. an aqueous component;
wherein the composite material has a pH of 3 or lower.

2. The material of claim 1, wherein the first gel component further comprises by weight percentage of the first gel component, from about 0.5 percent to about 1.0 percent salt.

3. The material of claim 1, wherein the dry cellulose material has a localized pH in a range of from about 2 to about 3.

4. The material of claim 1, wherein the carboxymethylcellulose has a molecular weight average of about 25 kDa with a 0.7 substitution.

5. The material of claim 1, wherein the composite material comprises by weight of the composite material:
   i. from about 25 percent to about 80 percent of the first gel component; and
   ii. from about 0.1 to about 25 percent of the second powder component.

6. The material of claim 1, wherein the second powder component comprises lyophilized oxidized regenerated cellulose.

7. The material of claim 1, wherein the composite material is a sterile, flowable gel.

8. A composite material comprising a mixture of:
   i. a first gel component, the first gel component comprising carboxymethyl cellulose having a molecular weight average of about 100 to about 300 kDa in an amount of from about 3 to about 6 percent by weight of the first gel component;
   ii. a second powder component comprising a dry cellulose material; and
   iii. an aqueous component;
wherein the composite material;
   a. has a pH of 3 or lower; and
   b. is a sterile, flowable gel.

9. The material of claim 8, wherein the first gel component further comprises by weight percentage of the first gel component, from about 0.5 percent to about 1.0 percent salt.

10. The material of claim 8, wherein the dry cellulose material is in the form of fibers.

11. The material of claim 8, wherein the dry cellulose material comprises oxidized regenerated cellulose microfibers having a localized pH of about 2.5 to about 4.5.

12. The material of claim 8, wherein the dry cellulose material has a localized pH in a range of from about 2 to about 3.

13. The material of claim 8, wherein the carboxymethylcellulose has a molecular weight average of about 25 kDa with a 0.7 substitution.

14. The material of claim 8, wherein the composite material comprises by weight of the composite material:
   i. from about 25 percent to about 80 percent of the first gel component; and
   ii. from about 0.1 to about 25 percent of the second powder component.

15. The material of claim 8, wherein the second powder component comprises lyophilized oxidized regenerated cellulose.

16. A composite material having a pH of 3 or lower, the composite material comprising a mixture of:
   i. a first gel component, the first gel component comprising carboxymethyl cellulose;
   ii. a second powder component comprising a dry cellulose material and having a localized pH in a range of about 2 to about 3; and
   iii. an aqueous component.

17. The material of claim 16, wherein the first gel component comprises carboxymethyl cellulose having a molecular weight average of about 100 to about 300 kDa in an amount of about 3 to about 6 percent by weight of the first gel component.

18. The material of claim 16, wherein the first gel component further comprises by weight percentage of the first gel component, from about 0.5 percent to about 1.0 percent salt.

19. The material of claim 16, wherein the dry cellulose material is in the form of micro-fibers.

20. The material of claim 16, wherein the second powder component comprises lyophilized oxidized regenerated cellulose.

* * * * *